(12) United States Patent
Chao (10) Patent No.: US 10,004,663 B2
(45) Date of Patent: Jun. 26, 2018

(54) ELECTROTHERAPY SYSTEM FOR TRADITIONAL CHINESE MEDICINE

(71) Applicant: Kuang-Cheng Chao, New Taipei (TW)

(72) Inventor: Kuang-Cheng Chao, New Taipei (TW)

(*) Notice: Subject to any disclaimer, the term of this patent is extended or adjusted under 35 U.S.C. 154(b) by 0 days. days.

(21) Appl. No.: 15/234,797

(22) Filed: Aug. 11, 2016

(65) Prior Publication Data

US 2017/0071823 A1 Mar. 16, 2017

(30) Foreign Application Priority Data

Sep. 16, 2015 (TW) .............................. 104130534 A (51) Int. Cl.
| | |
|---|---|
| *A61H 39/02* | (2006.01) |
| *A61H 39/00* | (2006.01) |
| *A61N 1/04* | (2006.01) |
| *A61N 1/20* | (2006.01) |
| *A61N 1/36* | (2006.01) |
| *A61B 5/024* | (2006.01) |
| *A61B 5/022* | (2006.01) |
| *G16H 10/60* | (2018.01) |

(Continued)

(52) U.S. Cl.
CPC ............ *A61H 39/002* (2013.01); *A61B 5/022* (2013.01); *A61B 5/024* (2013.01); *A61B 5/4854* (2013.01); *A61N 1/0456* (2013.01); *A61N 1/0492* (2013.01); *A61N 1/205* (2013.01); *A61N 1/36014* (2013.01); *G16H 10/60* (2018.01); *A61B 5/0015* (2013.01); *A61B 5/04085* (2013.01); *A61B 5/7235* (2013.01); *A61H 2201/0157* (2013.01); *A61H 2201/10* (2013.01); *A61H 2201/165* (2013.01); *A61H 2201/1688* (2013.01); *A61H 2201/5005* (2013.01); *A61H 2201/5007* (2013.01); *A61H 2201/5035* (2013.01); *A61H 2201/5043* (2013.01); *A61H 2201/5076* (2013.01); *A61H 2201/5097* (2013.01); *A61H 2230/06* (2013.01); *A61H 2230/08* (2013.01); *A61H 2230/30* (2013.01); *H04M 1/72527* (2013.01)

(58) Field of Classification Search
CPC .. A61H 39/002; A61B 5/4047; A61N 1/0492; A61N 1/205; A61N 1/36014; A61N 5/0619

See application file for complete search history.

(56) References Cited

U.S. PATENT DOCUMENTS

| | | | |
|---|---|---|---|
| 2004/0044384 A1* | 3/2004 | Leber ................... | A61N 5/0619 607/88 |
| 2008/0091248 A1* | 4/2008 | Libbus ............... | A61N 1/36014 607/60 |

FOREIGN PATENT DOCUMENTS

TW M488321 U 10/2014

* cited by examiner

*Primary Examiner* — Paula J Stice
(74) *Attorney, Agent, or Firm* — Hamre, Schumann, Mueller & Larson, P.C.

(57) ABSTRACT

An electrotherapy system includes a control device, a pulse generator and an electrode pad unit. The control device receives a user input associated with one of twelve meridians of a human, and outputs a control signal associated with the one of the twelve meridians. The pulse generator generates an electrical stimulation signal according to a reference frequency of a reference signal and the one of the twelve meridians with which the control signal is associated. The electrode pad unit contacts a user at a location corresponding to the one of the twelve meridians, and is coupled to the pulse generator for introducing the electrical stimulation signal from the pulse generator to the user.

14 Claims, 6 Drawing Sheets

(51) Int. Cl.
*H04M 1/725* (2006.01)
*A61B 5/00* (2006.01)
*A61B 5/0408* (2006.01)

FIG.5

ELECTROTHERAPY SYSTEM FOR TRADITIONAL CHINESE MEDICINE

CROSS-REFERENCE TO RELATED APPLICATION

This application claims priority of Taiwanese Patent Application No. 104130534, filed on Sep. 16, 2015.

FIELD

The disclosure relates to an electrotherapy system, and more particularly to an electrotherapy system for traditional Chinese medicine.

BACKGROUND

Transcutaneous electrical nerve stimulation (TENS) is an alternative treatment for muscle soreness and muscle pain to massage.

Most currently available TENS apparatuses, such as one disclosed in Taiwanese Patent No. M488321, are designed based on theories of western medicine, and the intensity and frequency of the stimulation outputted thereby are user adjustable. Stimulation with low frequency (e.g., <10 Hz) current could enhance secretion of Endorphin and alleviate the feeling of pain. Stimulation with higher frequency (e.g., >100 Hz) current could block transmission of pain signals by inducing pre-synaptic inhibition on thick and thin afferent nerve fibers which form synapses with transmission cells, so that the pain is suppressed. In practice, composite electrical stimulation, where currents of different frequencies are alternately outputted, is commonly used to relieve pain.

From the perspective of traditional Chinese medicine, pain results from blood stasis, a phenomenon in which circulation of qi and blood is inhibited inside the meridians. If not uninhibited in time, the inhibited qi and blood may eventually form poison and result in pain and discomfort. Therefore, facilitating the circulation of qi and blood in the meridians would relieve or eliminate the pain and feelings of discomfort.

SUMMARY

Therefore, an object of the disclosure is to provide an electrotherapy system for traditional Chinese medicine.

The electrotherapy system includes a control device, a pulse generator and an electrode pad unit. The control device includes a user interface configured to receive a first user input associated with one of twelve meridians of a human, and a control module configured to output a control signal associated with the one of the twelve meridians according to the first user input. The pulse generator is coupled to the control module for receiving therefrom the control signal, is disposed to receive a reference signal associated with a reference frequency, and is configured to generate an electrical stimulation signal according to the reference frequency and the one of the twelve meridians. The electrode pad unit is to contact a user at a location corresponding to the one of the twelve meridians, and is coupled to the pulse generator for introducing the electrical stimulation signal from the pulse generator to the user.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Before the disclosure is described in greater detail, it should be noted that where considered appropriate, reference numerals or terminal portions of reference numerals have been repeated among the figures to indicate corresponding or analogous elements, which may optionally have similar characteristics.

Figure 1:
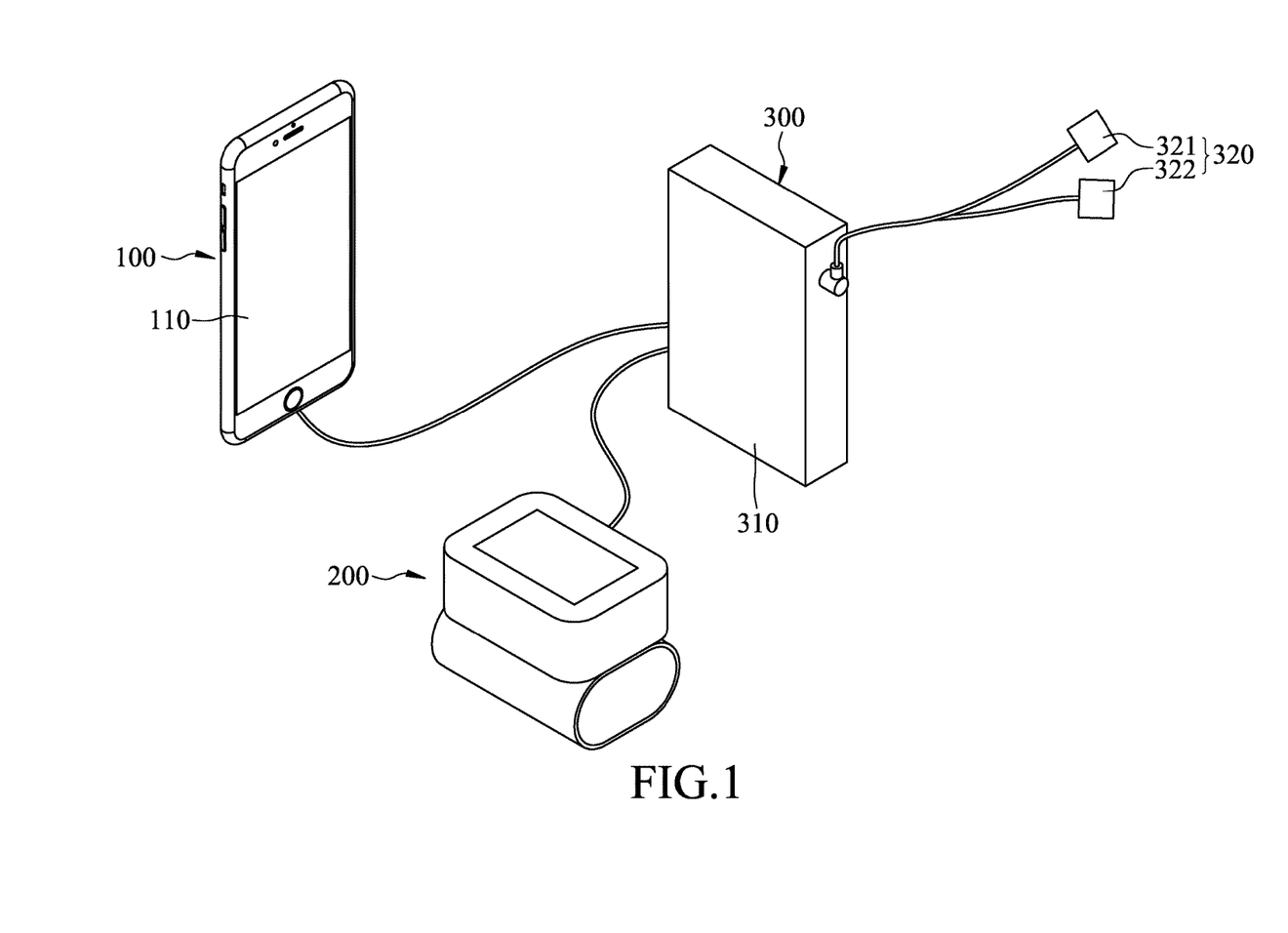
FIG. 1 is a perspective view illustrating an embodiment of an electrotherapy system according to the disclosure.
Figure 2A:
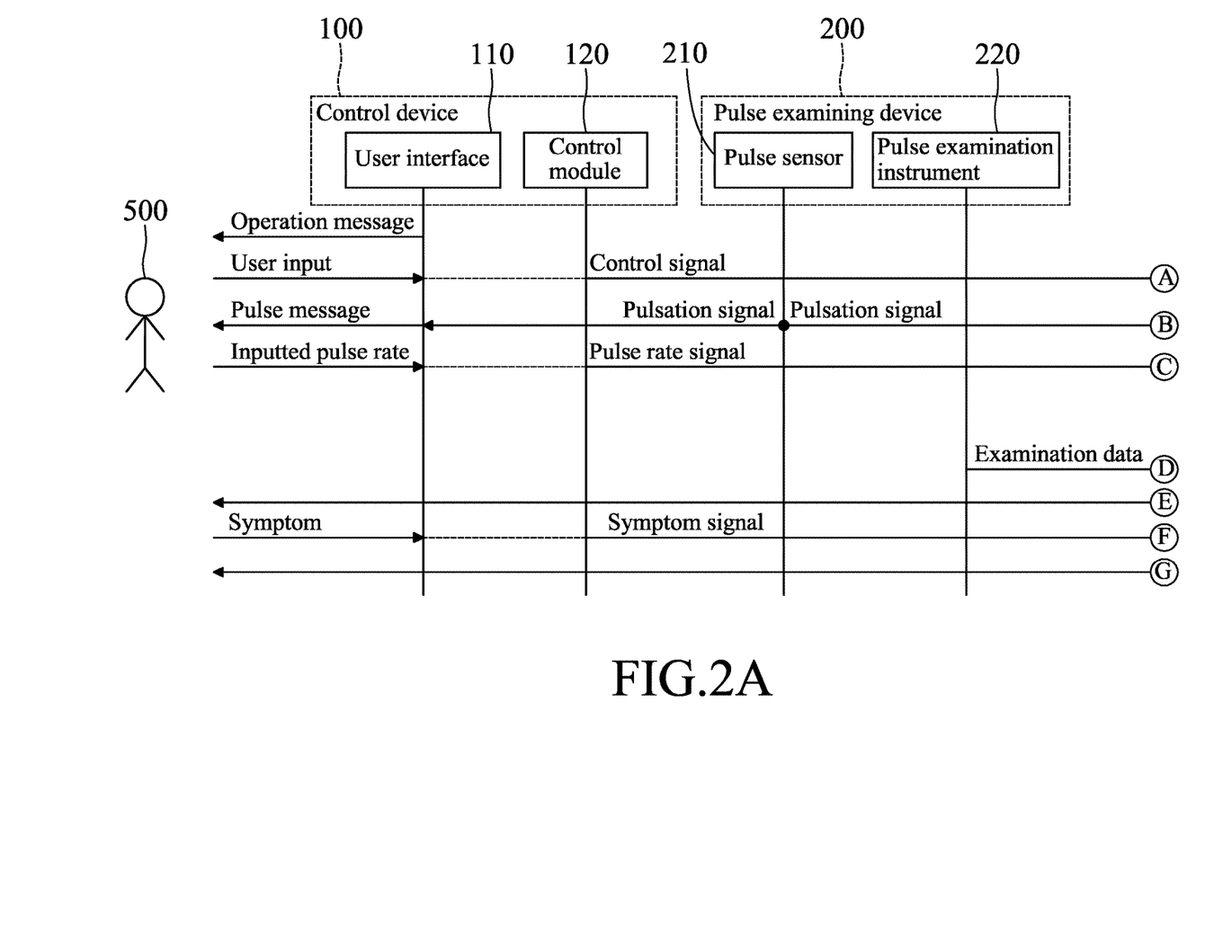
FIGS. 2A and 2S are a schematic diagram illustrating signal transmission of the embodiment.
Figure 2B:
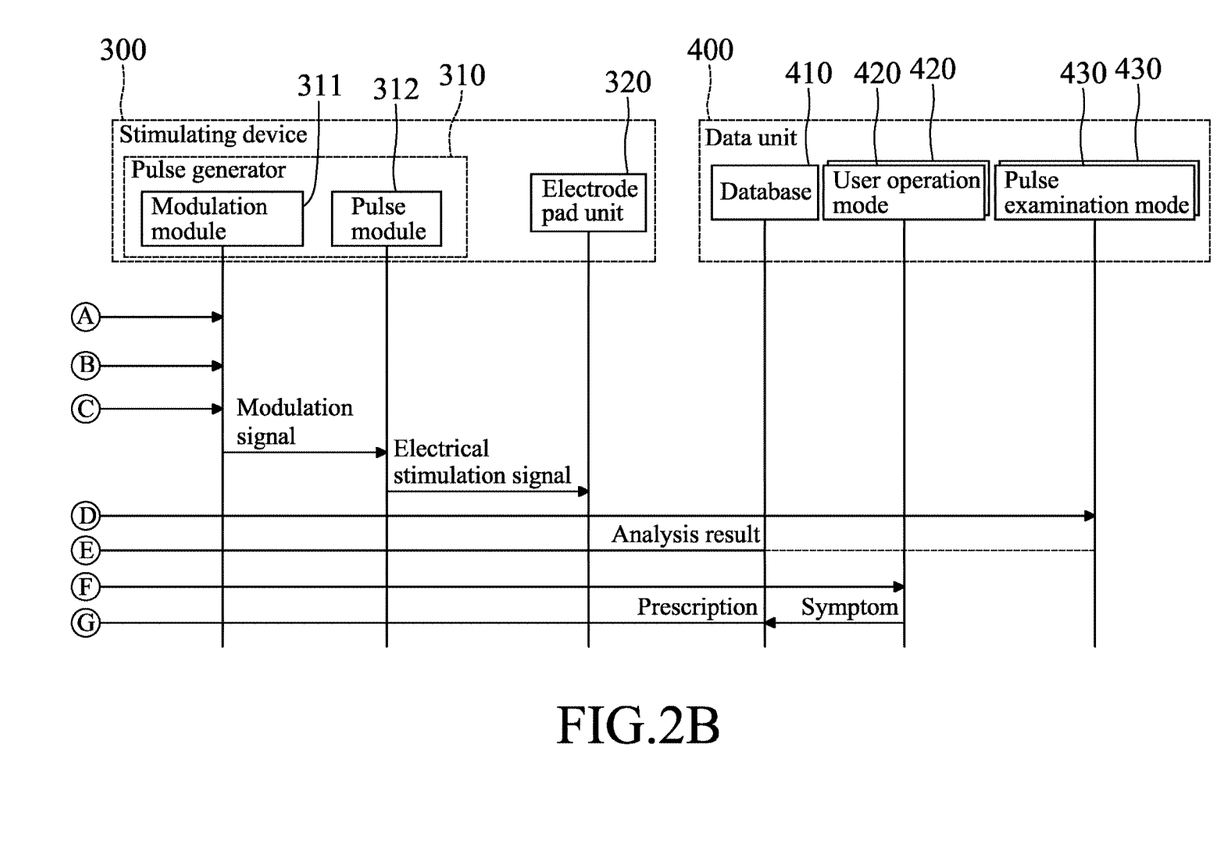

Referring to FIGS. 1, 2A and 2B, the embodiment of an electrotherapy system for facilitating circulation of qi and blood in meridians is illustrated. The electrotherapy system includes a control device 100, a pulse examining device 200, a stimulating device 300 and a data unit 400. In this embodiment, the control device 100, the pulse examining device 200, and the stimulating device 300 are communicatively coupled to each other, and the data unit 400 is communicatively coupled to the control device 100 and the pulse examining device 200, but this disclosure is not limited thereto.

Figure 3:
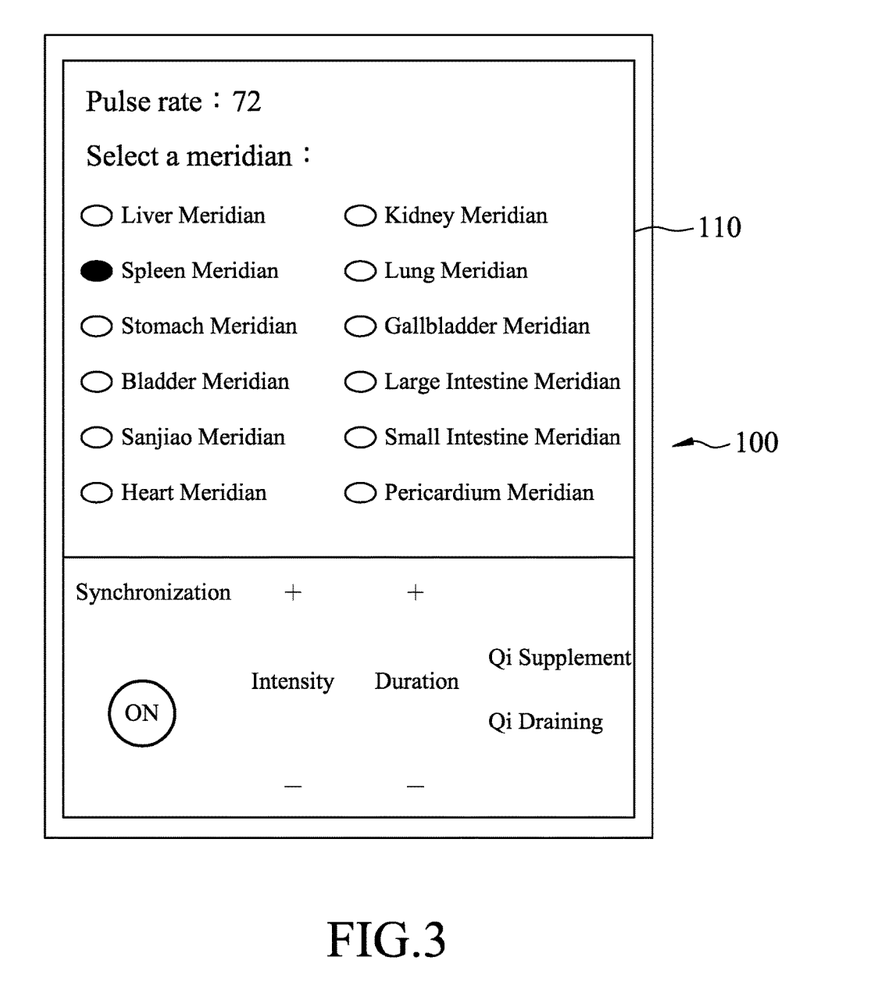
FIG. 3 is a schematic diagram illustrating an exemplary user interface according to the disclosure.

The control device 100 includes a user interface 110 and a control module 120. As illustrated in FIG. 3, the user interface 110 is configured to display a first operation message associate with twelve meridians of a human, a second operation message associated with a qi supplement mode and a qi draining mode. Referring to FIGS. 1, 2A and 2B again, the user interface 110 is further configured to receive user inputs associated with the first and second operation messages. In practice, a user 500 may employ the user interface 110 to select one of the twelve meridians in the first operation message to serve as a first user input, and to select one of the qi supplement mode and the qi draining mode in the second operation message to serve as a second user input. The control module 120 is configured to output a control signal associated with the selected one of the twelve meridians and the selected one of the qi supplement mode and the qi draining mode.

Modern-day smartphones, smartwatches and the like are usually equipped with high-performance processors, multi-functional sensors, various apps (applications), and Internet accessibility. Such devices are suitable for implementing the control device 100 of this disclosure. In this embodiment, the control device 100 is a smartphone, but it can also be a desktop computer, a laptop computer, a tablet computer, a smart TV, or a smartwatch in other embodiments. In this embodiment, a screen of the smartphone serves as the user interface 110, and the messages displayed thereon depends on apps installed in the smartphone. In this embodiment, the messages are in text form, and may be in graphic form in other embodiments, such as a diagrammatic sketch of twelve meridians of a human, so that a more intuitive operation is enabled.

The pulse examining device 200 includes a pulse sensor 210 and a pulse examination instrument 220. It is noted that the electrotherapy system of this disclosure is developed to enhance resonance of organ(s) with a frequency associated with a heartbeat frequency. Accordingly, the pulse sensor 210 is used to sense arterial pulsation of the user 500 automatically, and to output to the control device 100 and the stimulating device 300 a pulsation signal that has a pulsation frequency and a pulsation phase according to the arterial pulsation thus sensed, and then the user interface 110 may display a pulse message indicating a pulse rate (i.e., the pulsation frequency) according to the arterial pulsation sensed by the pulse examining device 200. In this embodiment, when the pulse sensor 210 malfunctions and/or is unable to output the pulsation signal, the user interface 110 may be used to input manually a desired pulse rate, and the control module 120 may further output to the stimulating device 300 a pulse rate signal associated with the pulse rate thus inputted. In a case that the pulse rate is manually inputted by the user 500, the pulse message displayed by the user interface 110 may indicate the pulse rate thus inputted. The pulse examination instrument 220 is configured to perform pulse examination on meridians of the user 500, and to output to the data unit 400 a result of the pulse examination thus performed (i.e., a pulse condition of the user 500) for analysis and assessment. Because the pulse examination instrument 220 is not the focus of this disclosure, details thereof are omitted herein for the sake of brevity.

The stimulating device 300 includes a pulse generator 310, and an electrode pad unit 320 coupled to the pulse generator 310. The pulse generator 310 includes a modulation module 311 and a pulse module 312. The modulation module 311 is coupled to the control module 120 for receiving therefrom the control signal and the pulse rate signal, is coupled to the pulse examining device 200 for receiving therefrom the pulsation signal, and is configured to select one of the pulsation signal and the pulse rate signal to serve as a reference signal, and to output to the pulse module 312 a modulation signal according to the control signal and the reference signal.

In detail, when the pulsation signal serves as the reference signal, the modulation module 311 analyzes the pulsation signal for acquiring therefrom the pulsation phase and the pulsation frequency, and then generates the modulation signal according to the control signal, the pulsation frequency and the pulsation phase. Lastly, the pulse module 312 outputs to the electrode pad unit 320 an electrical stimulation signal corresponding to the modulation signal for transcutaneous stimulation. The muscles under the stimulated skin will contract intermittently and resonate with relevant meridians. It is noted that, in this case, the pulsation frequency serves as a reference frequency for generation of the modulation signal.

In a case that the pulse rate signal serves as the reference signal, the modulation module 311 acquires the inputted pulse rate from the pulse rate signal to serve as the reference frequency for generation of the modulation signal. The modulation module 311 makes the reference frequency a fundamental frequency to perform frequency modulation, determines an integer according to the one of the twelve meridians with which the first user input is associated, and to generate the modulation signal having a frequency which is the integer multiple of the fundamental frequency.

According to a theory of resonant blood circulation proposed by Dr. Wei Kung Wang, each organ/artery has a natural frequency, and harmonics of a heartbeat signal, generated by output from the heart, constitute an orthogonal basis for representing blood pressure wave. The blood pressure comprising harmonic driving force drives blood into the organs through the arteries. Depending on different matching conditions between the heartbeat and the natural frequencies of the arterial system, harmonic spectrum of the blood pressure wave varies. When a harmonic component of the blood pressure wave is near one of the natural frequencies of the arterial system, i.e., in a frequency-matching condition, amplitude of the harmonic component will be greatly enhanced because of resonance, and hence, efficient blood delivery is achieved. Similarly, frequency matching between an organ and an artery with which the organ is connected facilitates blood delivery. As a result, organs are developed to be resonant with the heartbeats for efficient blood delivery. In Traditional Chinese Medicine, twelve meridians have been discovered and each meridian is a highway for transporting harmonics of a certain blood pressure wave in the human body. The twelve meridians allow twelve harmonics and the blood to move to corresponding organs and resonant organs with the same harmonics. The twelve meridians and the corresponding harmonics are:

(1) Liver Meridian of Foot-Jueyin corresponding to a first harmonic;

(2) Kidney Meridian of Foot-Shaoyin corresponding to a second harmonic;

(3) Spleen Meridian of Foot-Taiyin corresponding to a third harmonic;

(4) Lung Meridian of Hand-Taiyin corresponding to a fourth harmonic;

(5) Stomach Meridian of Foot-Yangming corresponding to a fifth harmonic;

(6) Gallbladder Meridian of Foot-Shaoyang corresponding to a sixth harmonic;

(7) Bladder Meridian of Foot-Taiyang corresponding to a seventh harmonic;

(8) Large Intestine Meridian of Hand-Yangming corresponding to an eighth harmonic;

(9) Sanjiac Meridian of Hand-Shaoyang corresponding to a ninth harmonic;

(10) Small Intestine Meridian of Hand-Taiyang corresponding to a tenth harmonic;

(11) Heart Meridian of Hand-Shaoyin corresponding to an eleventh harmonic; and (12) Pericardium Meridian of Hand-Jueyin corresponding to harmonic zero.

For example, if the heart beats at 1.2 Hz, the first harmonic corresponding to the Liver Meridian of Foot-Jueyin will have a frequency of 1.2 Hz, the second harmonic corresponding to the Kidney Meridian of Foot-Shaoyin will have a frequency of 2.4 Hz, the third harmonic corresponding to the Spleen Meridian of Foot-Taiyin will have a frequency of 3.6 Hz, and so on. It is noted that the Pericardium Meridian of Hand-Jueyin is defined to correspond to the harmonic zero that is a DC signal representing a sum of energy of total harmonics.

Accordingly, the modulation signal as well as the corresponding electrical stimulation signal is a DC signal (i.e., the integer determined by the modulation module 311 is zero) when the one of the twelve meridians (which is selected by the user 500 through the user interface 110) is the Pericardium Meridian of Hand-Jueyin, and has: a first order harmonic frequency of the fundamental frequency when the one of the twelve meridians is the Liver Meridian of Foot-Jueyin (i.e., the integer determined by the modulation module 311 is one); a second order harmonic frequency of the fundamental frequency when the one of the twelve meridians is the Kidney Meridian of Foot-Shaoyin (i.e., the integer determined by the modulation module 311 is two); a third order harmonic frequency of the fundamental frequency when the one of the twelve meridians is the Spleen Meridian of Foot-Taiyin (i.e., the integer determined by the modulation module 311 is three); a fourth order harmonic frequency of the fundamental frequency when the one of the twelve meridians is the Lung Meridian of Hand-Taiyin (i.e., the integer determined by the modulation module 311 is four); a fifth order harmonic frequency of the fundamental frequency when the one of the twelve meridians is the Lung Meridian of Hand-Taiyin (i.e., the integer determined by the modulation module 311 is five); a sixth order harmonic frequency of the fundamental frequency when the one of the twelve meridians is the Gallbladder Meridian of Foot-Shaoyang (i.e., the integer determined by the modulation module 311 is six); a seventh order harmonic frequency of the fundamental frequency when the one of the twelve meridians is the Bladder Meridian of Foot-Taiyang (i.e., the integer determined by the modulation module 311 is seven); an eighth order harmonic frequency of the fundamental frequency when the one of the twelve meridians is the Large Intestine Meridian of Hand-Yangming (i.e., the integer determined by the modulation module 311 is eight); a ninth order harmonic frequency of the fundamental frequency when the one of the twelve meridians is the Sanjiao Meridian of Hand-Shaoyang (i.e., the integer determined by the modulation module 311 is nine); a tenth order harmonic frequency of the fundamental frequency when the one of the twelve meridians is the Small Intestine Meridian of Hand-Taiyang (i.e., the integer determined by the modulation module 311 is ten); and an eleventh order harmonic frequency of the fundamental frequency when the one of the twelve meridians is the Heart Meridian of Hand-Shaoyin (i.e., the integer determined by the modulation module 311 is eleven).

In this embodiment, the electrode pad unit 320 includes a positive electrode pad having a positive electrode 321 disposed thereon, an a negative electrode pad having a negative electrode 322 disposed thereon, and is configured to contact the user 500 at a location corresponding to the selected one of the twelve meridians, and to introduce the electrical stimulation signal from the pulse module 312 to the user 500. The positive and negative electrodes 321, 322 may be placed separately at a proper distance from each other on the skin of the user 500 along a path corresponding to one of the twelve meridians that is to be stimulated (i.e., the selected one of the twelve meridians), so that a weak current flows from the positive electrode 321 to the negative electrode 322 through the contacted skin, subcutaneous tissue, and muscle, and a current loop is thus formed.

Figure 5:
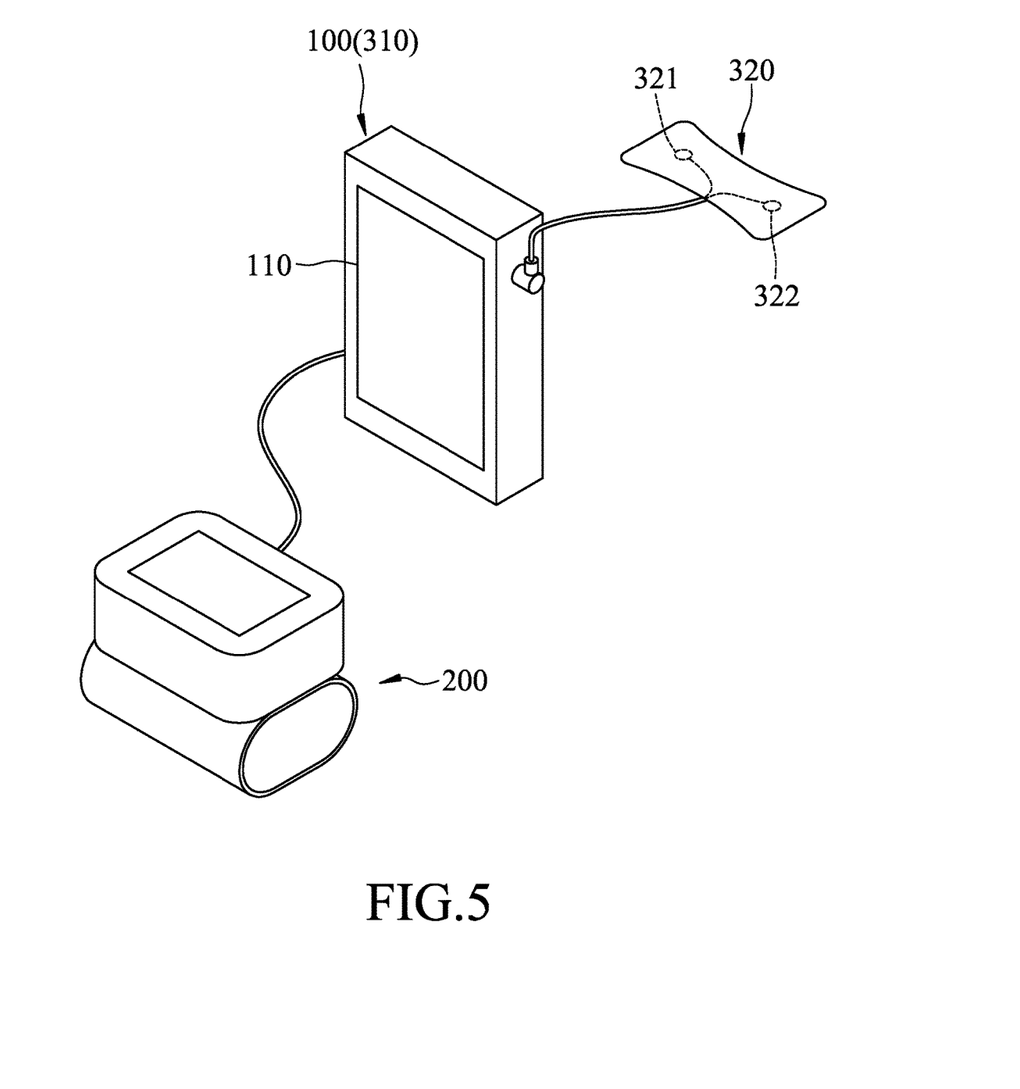
FIG. 5 is a schematic diagram illustrating a variation of the embodiment.

It is noted that if the positive and negative electrodes 321, 322 are placed too close to each other, the current loop may only form at skin surface between the electrodes 321, 322. If the positive and negative electrodes 321, 322 are placed too far from each other, resistance between the electrodes 321, 322 may be too large to induce sufficient current for muscle stimulation. For ease of use, a variation of the electrode pad unit 320 is shown in FIG. 5, and includes only one electrode pad on which the positive electrode 321 and the negative electrode 322 are disposed. A distance between the positive and negative electrodes 321, 322 is determined based on output power of the pulse generator 310. For a pulse generator 310 with higher power, the distance between the positive electrode 321 and the negative electrode 322 could be longer to stimulate more muscles. On the other hand, a pulse generator 310 with lower power may be suitable for stimulating acupuncture points over the meridians. Based on experiments, a preferred distance between the positive electrode 321 and the negative electrode 322 is, but not limited to, between 4 and 7 cm. It is noted that, in FIG. 5, the control device 100 and the pulse generator 310 is integrated together as a single device, such as a smartphone. In this case, an output port of the smartphone, such as an audio jack, may be used for connection with the electrode pad unit 320. However, since the smartphone may be unable to provide sufficient output current for stimulation, a current amplifier (not shown) may be necessary. Since current amplification is not the feature of the disclosure, details thereof are omitted herein for the sake of brevity.

The driving force in resonant blood circulation is called qi in traditional Chinese medicine. If resonance property of an organ deviates from its normal condition such that the natural frequency of the organ is shifted away from a particular harmonic component of the heartbeat signal, blood delivery into the organ will become inefficient. Abnormal transportation of oxygen, nutrients, and metabolic waste will arise and consequently cause an illness called qi deficiency. Also, weak heartbeats would cause abnormal blood delivery and eventually lead to diseases. In addition, diseases affecting organs corresponding to lower harmonics may adversely affect organs corresponding to higher harmonics. Such phenomenon corresponds to the concepts of internal-external relations and allelopathy in traditional Chinese medicine. Through adjusting the resonance property of the meridians as proposed in this disclosure and under the guidance of the theory of visceral manifestation in traditional Chinese medicine, traditional Chinese medicine physicians would be able to perform treatment on patients based on syndrome differentiation.

It is noted that the phenomenon of interference exists in qi in traditional Chinese medicine as well as in waves in physics. Qi supplement and qi draining in traditional Chinese medicine respectively correspond to increase and decrease of oscillation amplitudes of the meridians. Accordingly, when the user 500 selects the qi supplement mode through the user interface 110 (i.e., the second user input being associated with the qi supplement mode), the pulse generator 310 outputs the electrical stimulation signal with a stimulation phase forming constructive interference with the pulsation phase of the pulsation signal by phase superposition, so that the oscillation amplitude of the selected one of the twelve meridians may be enhanced. On the other hand, when the user 500 selects the qi draining mode through the user interface 110 (i.e., the second user input being associated with the qi draining mode), the pulse generator 310 outputs the electrical stimulation signal with a stimulation phase forming destructive interference with the pulsation phase of the pulsation signal by phase superposition, so that the oscillation amplitude of the selected one of the twelve meridians may be mitigated. For example, referring to FIG. 4 where it is exemplified that the qi supplement mode and the Spleen Meridian of Foot-Taiyin are selected through the user interface 110, the upper plot illustrates a waveform of the pulsation signal (i.e., the heartbeat signal of the user 500) outputted by the pulse sensor 210, and the lower plot illustrates a waveform of the electrical stimulation signal. As indicated in the upper plot, interbeat intervals of the first four consecutive heartbeats are respectively denoted by T1, T2, and T3, and the lower plot shows corresponding time intervals T1', T2', T3' for the electrical stimulation signal with a delay of a period of T0 which may result from processing delay of the stimulating device 300. Since the Spleen Meridian of Foot-Taiyin is selected, the electrical stimulation signal has the third order harmonic frequency of the fundamental frequency (i.e., triple the heartbeat frequency). In other words, the electrical stimulation signal has three pulses during each of time intervals T1', T2', T3' of the electrical stimulation signal that respectively correspond to the interbeat intervals T1, T2, and T3 of the heartbeat signal. It is noted that the pulse sensor 210 generating the pulsation signal, which serves as the reference signal, is a cardiograph in this embodiment, so the frequency of the electrical stimulation signal during different time intervals may vary due to change of the heartbeat frequency. However, if the reference signal is the pulse rate signal that results from a user input, or the pulsation signal generated by an ordinary heart rate monitor, the modulation signal and the resultant electrical stimulation signal may have a constant frequency and a constant pulse width.

Figure 4:
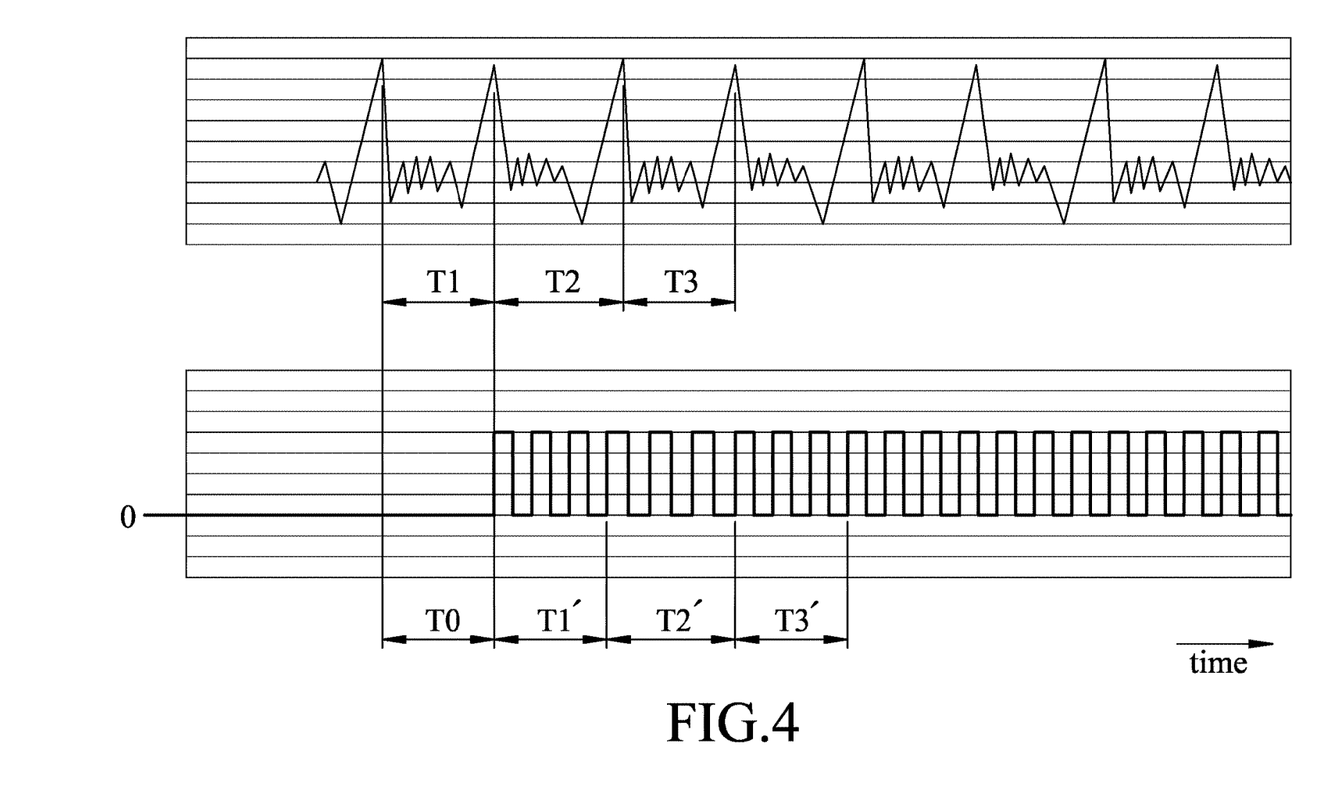
FIG. 4 is a schematic diagram showing a waveform of a heartbeat signal and a waveform of an electrical stimulation signal that has a harmonic frequency corresponding to the Spleen Meridian of Foot-Taiyin.

Moreover, in the qi supplement mode, in order to induce constructive interference, the electrical stimulation signal is generated to have a high voltage level at a time point corresponding to a peak of the pulsation signal/heartbeat signal (see FIG. 4). Similarly, in the qi draining mode, in order to induce destructive interference, the electrical stimulation signal is generated to have a low voltage level at a time point corresponding to a peak of the pulsation signal/heartbeat signal (not shown). Also, intensity of the electrical stimulation signal may be adjustable by the user 500 or programmable according to personalization properties and on sensitivities of different parts of the body. Higher intensity would induce greater current that may penetrate deeper tissues so that a stronger effect of meridian stimulation is achieved.

Referring to FIGS. 2A, 2B and 3, the data unit 400 has a database 410, a plurality of predetermined user operation modes 420, and a plurality of predetermined pulse examination modes 430. Each of the predetermined user operation modes 420 corresponds to an individual symptom of poor circulation of qi and blood. In one embodiment, the user interface 110 is further configured to receive a third user input associated with a symptom of poor circulation of qi and blood, and the control device 100 outputs to the data unit 400 a symptom signal associated with the symptom of poor circulation of qi and blood according to the third user input. The data unit 400 is configured to retrieve from the database 410 a prescription corresponding to the symptom of poor circulation of qi and blood by operating in one of the predetermined user operation modes 420 that corresponds to the symptom of poor circulation of qi and blood with which the symptom signal is associated, and to output the prescription thus retrieved to the control device 100 for display by the user interface 110, so that the user 500 may perform stimulation according to the prescription for alleviating the symptom of poor circulation of qi and blood. In addition, the data unit 400 may receive from the pulse examination instrument 220 the result of the pulse examination (called examination data hereinafter), retrieve from the database 410 an analysis result associated with improving circulation of qi and blood by operating in one of the predetermined pulse examination modes 430 that corresponds to the examination data, and output the analysis result thus retrieved to the control device 100 for display by the user interface 110. Moreover, the data unit 400 may be implemented as an application stored in a memory unit (not shown) of the control device 100, or be implemented using a cloud storage system (not shown). Therefore, portable/wearable devices such as smartphones or smartwatches may be utilized to implement the control device 100, the pulse examining device 200 and the data unit 400, and to output the control signal and the pulsation signal/pulse rate signal to the pulse generator 310 by wired or wireless transmission. Further, the aforementioned prescription and/or analysis result may be acquired through the Internet or one or more installed apps. Using the cloud storage system (not shown) may facilitate management and analysis of user-related information, such as a record of usage history, retrieval of information of relevant symptoms, examination data outputted by the pulse examining device 200, etc., for personalized health information management, preventing loss of data, and easing integration with relevant medical application(s).

To sum up, through setting the control signal via the user interface 110, a modulation signal corresponding to a selected meridian and a selected one of the qi supplement mode and the qi draining mode may be outputted to the pulse module 312, which generates a corresponding electrical stimulation signal to be outputted to the electrode pad unit 320. Subsequently, muscles stimulated by the electrical stimulation signal outputted by the electrode pad unit 320 would intermittently contract to adjust resonance of the corresponding meridian, and the circulation of qi and blood in the meridian may thus be facilitated.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. An electrotherapy system for traditional Chinese medicine comprising:
   a control device, the control device including:
      a user interface configured to receive a first user input associated with one of twelve meridians of a human; and
      a control module coupled to said user interface and configured to receive the first user input therefrom, the control module being configured to output a control signal indicating the one of the twelve meridians according to the first user input;
   a pulse examining device;
   a pulse generator coupled to said control module and configured to receive therefrom the control signal, the pulse generator being coupled to the pulse examining device, the pulse generator being configured to receive a reference signal containing information of a reference frequency from either said control module or said pulse examining device, said pulse generator being configured to generate an electrical stimulation signal based on the reference frequency, and the electrical stimulation signal having a predetermine parameter corresponding to the one of the twelve meridians which is indicated by the control signal; and an electrode pad unit configured to contact a user at a location corresponding to the one of the twelve meridians, coupled to said pulse generator and configured to introduce the electrical stimulation signal from said pulse generator to the user.

2. The electrotherapy system for traditional Chinese medicine of claim 1, wherein said pulse examining device includes a pulse sensor coupled to said pulse generator, and
the pulse sensor is configured to sense arterial pulsation of the user, and to output, according to the arterial pulsation thus sensed, to said pulse generator a pulsation signal having a pulsation frequency,
wherein said pulse generator is further configured to make the pulsation signal serve as the reference signal, and to acquire from the pulsation signal the pulsation frequency to serve as the reference frequency.

3. The electrotherapy system for traditional Chinese medicine of claim 2, wherein:
said user interface is further configured to receive a second user input associated with one of a qi supplement mode and a qi draining mode;
the control signal outputted by said control module further indicates the one of the qi supplement mode and the qi draining mode according to the second user input; and
said pulse generator is further configured to acquire from the pulsation signal a time point of a positive peak in a cycle of the pulsation signal the pulsation phase, and to generate the electrical stimulation signal, the electrical stimulation signal forming constructive interference with the pulsation signal phase by phase superposition when the control signal indicates the qi supplement mode, and forming destructive interference with the pulsation signal phase by phase superposition when the control signal indicates the qi draining mode,
wherein the qi supplement mode is a user input that indicates an increase of an oscillation amplitude of the one of the twelve meridians, and the qi draining mode is a user input that indicates a decrease of the oscillation amplitude of the one of the twelve meridians.

4. The electrotherapy system for traditional Chinese medicine of claim 3, wherein:
said pulse sensor is further configured to output the pulsation signal to said control device; and
said user interface is further configured to display a first operation message associate with the twelve meridians for user operation, a second operation message associated with the qi supplement mode and the qi draining mode for user operation, and a pulse message associated with the pulsation signal.

5. The electrotherapy system for traditional Chinese medicine of claim 2, wherein:
said user interface is further configured to receive a pulse rate input associated with a pulse rate;
said control module is further configured to output to said pulse generator a pulse rate signal that indicates the pulse rate; and
said pulse generator is further configured to selectively select one of the pulsation signal and the pulse rate signal to serve as the reference signal, to make the pulsation frequency serve as the reference frequency when the pulsation signal serves as the reference signal, and to make the pulse rate indicated by the pulse rate signal serve as the reference frequency when the pulse rate signal serves as the reference signal.

6. The electrotherapy system for traditional Chinese medicine of claim 1, wherein said pulse generator is further configured to make the reference frequency serve as a fundamental frequency, to determine an integer according to the one of the twelve meridians, and to generate the electrical stimulation signal that has a frequency which is the integer multiple of the fundamental frequency.

7. The electrotherapy system for traditional Chinese medicine of claim 1, wherein said pulse generator is further configured to make the reference frequency serve as a fundamental frequency, and to generate the electrical stimulation signal that is a direct current (DC) signal when the one of the twelve meridians is a Pericardium Meridian of Hand-Jueyin, and that has:
a first order harmonic frequency of the fundamental frequency when the one of the twelve meridians is a Liver Meridian of Foot-Jueyin;
a second order harmonic frequency of the fundamental frequency when the one of the twelve meridians is a Kidney Meridian of Foot-Shaoyin;
a third order harmonic frequency of the fundamental frequency when the one of the twelve meridians is a Spleen Meridian of Foot-Taiyin;
a fourth order harmonic frequency of the fundamental frequency when the one of the twelve meridians is a Lung Meridian of Hand-Taiyin;
a fifth order harmonic frequency of the fundamental frequency when the one of the twelve meridians is a Lung Meridian of Hand-Taiyin;
a sixth order harmonic frequency of the fundamental frequency when the one of the twelve meridians is a Gallbladder Meridian of Foot-Shaoyang;
a seventh order harmonic frequency of the fundamental frequency when the one of the twelve meridians is a Bladder Meridian of Foot-Taiyang;
an eighth order harmonic frequency of the fundamental frequency when the one of the twelve meridians is a Large Intestine Meridian of Hand-Yangming;
a ninth order harmonic frequency of the fundamental frequency when the one of the twelve meridians is a Sanjiao Meridian of Hand-Shaoyang;
a tenth order harmonic frequency of the fundamental frequency when the one of the twelve meridians is a Small Intestine Meridian of Hand-Taiyang; and
an eleventh order harmonic frequency of the fundamental frequency when the one of the twelve meridians is a Heart Meridian of Hand-Shaoyin.

8. The electrotherapy system for traditional Chinese medicine of claim 1, wherein:
said user interface is further configured to receive a pulse rate input associated with a pulse rate;
said control module is further configured to output to said pulse generator a pulse rate signal that indicates the pulse rate; and
said pulse generator is further configured to make the pulse rate signal serve as the reference signal, and to make the pulse rate serve as the reference frequency.

9. The electrotherapy system for traditional Chinese medicine of claim 1, wherein said electrode pad unit includes one electrode pad that has a positive electrode and a negative electrode disposed thereon.

10. The electrotherapy system for traditional Chinese medicine of claim 1, wherein said electrode pad unit includes a positive electrode pad having a positive electrode disposed thereon, and a negative electrode pad having a negative electrode disposed thereon.

11. The electrotherapy system for traditional Chinese medicine of claim 1, further comprising a data unit that has a database, and a plurality of predetermined user operation modes built therein, each of said predetermined operation modes corresponding to an individual symptom of poor circulation of qi and blood, wherein:

said user interface is further configured to receive a second user input associated with a symptom of poor circulation of qi and blood, and said control device is further configured to output to said data unit a symptom signal associated with the symptom of poor circulation of qi and blood according to the second user input; and said data unit is configured to retrieve from said database a prescription corresponding to the symptom of poor circulation of qi and blood by operating in one of said predetermined user operation modes that corresponds to the symptom of poor circulation of qi and blood with which the symptom signal is associated, and to output the prescription thus retrieved to said control device for display by said user interface.

12. The electrotherapy system for traditional Chinese medicine of claim 11, wherein said data unit is disposed to receive examination data, further has a plurality of predetermined pulse examination modes, and is configured to retrieve from said database an analysis result associated with improving circulation of qi and blood by operating in one of said predetermined pulse examination modes that corresponds to the examination data, and to output the analysis result thus retrieved to said control device for display by said user interface.

13. The electrotherapy system for traditional Chinese medicine of claim 12, further comprising a pulse examination instrument configured to perform pulse examination on meridians of the user, and to output to said data unit a result of the pulse examination thus performed to serve as the examination data.

14. The electrotherapy system for traditional Chinese medicine of claim 1 wherein said pulse generator is integrated in said control device.

* * * * *